United States Patent [19]

Esch et al.

[11] Patent Number: 5,484,581
[45] Date of Patent: Jan. 16, 1996

[54] PROCESS FOR THE PRODUCTION OF PRECIPITATED SILICA

[75] Inventors: Heinz Esch, Bonn; Robert Kuhlmann, Erftstadt; Mattias Neumueller, Hasselroth; Karin Otto, Hanau; Ralf Rausch, Kreuzau, all of Germany

[73] Assignee: Degussa Aktiengesellschaft, Frankfurt, Germany

[21] Appl. No.: 285,672

[22] Filed: Aug. 4, 1994

[30] Foreign Application Priority Data

Aug. 7, 1993 [DE] Germany .......... 43 26 576.6
Jul. 5, 1994 [DE] Germany .......... 44 23 493.7

[51] Int. Cl.⁶ .......... A61K 7/16; A61K 7/18; C09K 3/14; C01B 33/12
[52] U.S. Cl. .......... 423/335; 106/35; 51/308; 424/49
[58] Field of Search .......... 424/49; 106/35; 423/335, 339; 51/308

[56] References Cited

U.S. PATENT DOCUMENTS

| | | | |
|---|---|---|---|
| 3,235,331 | 2/1966 | Nauroth et al. | 51/308 |
| 3,928,540 | 12/1975 | Morgan | 423/335 |
| 3,977,893 | 8/1976 | Wason | 423/339 |
| 3,988,162 | 10/1976 | Wason | 423/339 |
| 4,067,746 | 1/1978 | Wason et al. | 423/335 |
| 4,076,549 | 2/1978 | Wason | 423/339 |
| 4,495,167 | 1/1985 | Nauroth et al. | 423/339 |
| 4,857,289 | 8/1989 | Nauroth et al. | 423/335 |
| 4,973,462 | 11/1990 | Akira et al. | 423/339 |
| 5,066,420 | 11/1991 | Chevallier | 423/339 |
| 5,110,574 | 5/1992 | Reinhardt et al. | 423/335 |
| 5,286,478 | 2/1994 | Persello | 424/49 |

FOREIGN PATENT DOCUMENTS

| | | |
|---|---|---|
| 0062749 | 10/1982 | European Pat. Off. . |
| 0315503 | 5/1989 | European Pat. Off. . |
| 0317378 | 5/1989 | European Pat. Off. . |
| 0407262 | 1/1991 | European Pat. Off. . |
| 1467019 | 7/1970 | Germany . |

*Primary Examiner*—Ronald W. Griffin
*Attorney, Agent, or Firm*—Beveridge, DeGrandi, Weilacher & Young

[57] ABSTRACT

Precipitated silica which has a BET surface area of 10–130 $m^2/g$, a CTAB surface area of 10–70 $m^2/g$, an average particle diameter of 5–20 μm, a Cu abrasion value in a 10% glycerol dispersion of 4–50 mg and thickening behavior in a CMC solution (20% dispersion) of 300–3500 mPa·s, is produced by simultaneously adding alkali silicate (weight modulus $SiO_2$:alkali oxide=2.5–3.9:1) and a mineral acid to an initial amount of water which has been adjusted to a pH value of 7.0 to 9.9 or 10.0 to 10.7 by the addition of water glass, holding the pH value constant between 7.0 and 9.9 or 10.0 to 10.7 during addition, wherein the initial precipitation temperature is 50°–90° C. and an increase in viscosity occurs after at most 25% of the duration of precipitation, adjusting the pH value to ≦6, preferably 3.5, once a silica content of greater than 120 g/l or greater than 150 g/l, preferably ≧160 g/l to 240 g/l, has been reached, separating the solid by filtration, washing, drying and grinding it. The precipitated silica may be used as an abrasive and/or thickening component in toothpastes.

11 Claims, 5 Drawing Sheets

PROCESS FOR THE PRODUCTION OF PRECIPITATED SILICA

INTRODUCTION AND BACKGROUND

The present invention relates to a process for the production of a precipitated silica.

Synthetically produced silicas have for many years played an important role as a constituent of dental care products. A range of processes for the production of silicas specially tailored for use in toothpastes is known. These processes are associated with processing disadvantages making them both economically and ecologically unsatisfactory.

In one type of process, large quantities of electrolytes are used which must subsequently be washed out again in order to achieve the necessary purity of the end product. This brings about a considerable salt loading of effluents (U.S. Pat. Nos 3,960,586 and 4,122,161 which are incorporated by reference in their entirety; DE-AS 24 46 038). Other processes incorporate additional partial stages to prepare particular initial precipitation mixtures or additional hydrothermal reaction stages with several isolation stages (U.S. Pat. No. 5,286,478 which is incorporated by reference in its entirety; EP-B 0 317 378).

A process for the production of a reinforcing precipitated silica with a surface area of above 200 m$^2$/g is known from DE-B 14 67 019. This precipitated silica is not suitable for use in toothpastes.

A further disadvantage of known processes is the low space-time yield during precipitation due to the necessary introduction of a stop interval (ageing stage) or by the use of dilute reaction components. In this manner, solids contents of only approximately 40–60 g SiO$_2$/l are customarily obtained on completion of precipitation (EP-B 0 317 378).

It has now surprisingly been found that it is possible to produce precipitated silicas in a single precipitation stage at a simultaneously elevated space-time yield and without adding electrolytes.

SUMMARY OF THE INVENTION

The present invention provides a process for the production of a precipitated silica which has a BET surface area of 10–130 m$^2$/g, a CTAB surface area of 10–70 m$^2$/g, an average particle diameter of 5–20 μm, a Cu abrasion value in a 10% glycerol dispersion of 4–50 mg, and thickening behavior in a CMC solution (20% dispersion) of 300–3500 mPa·s. The process involves simultaneously adding alkali metal silicate (weight modulus SiO$_2$:alkali metal oxide=2.5–3.9:1) and a mineral acid (e.g., sulfuric acid, HCl) to an initial amount of water which has been adjusted to a pH value of 7.0 to 9.9 or 10.0 to 10.7 by the addition of water glass (sodium silicate). The pH value is held constant between 7.0 and 9.9 or 10.0 to 10.7 during addition of the alkali metal silicate (e.g., sodium silicate, potassium silicate) and mineral acid. The initial precipitation temperature is 50°–90° C. and an increase in viscosity occurs after at most 25% of the duration of precipitation. The pH value is adjusted to ≦6, preferably 3.5, once a silica content of greater than 120 g/l or greater than 150 g/l, preferably ≧160 g/l to 240 g/l, has been reached, the solid is separated by filtration, washed, dried and ground. The process takes place in a single precipitation stage at a simultaneously elevated space-time yield and without adding electrolytes.

BRIEF DESCRIPTION OF THE DRAWINGS

The present invention will be further understood with reference to the drawings, wherein.

DETAILED DESCRIPTION OF THE INVENTION

The present invention provides a process for the production of a precipitated silica. The process involves simultaneously adding alkali metal silicate (weight modulus SiO$_2$:alkali metal oxide=2.5–3.9:1) and a mineral acid to an initial amount of water which has been adjusted to a pH value of 7.0 to 9.9 or 10.0 to 10.7 by the addition of water glass (sodium silicate). The pH value is held constant between 7.0 and 9.9 or 10.0 to 10.7 during addition of the alkali metal silicate and mineral acid. The initial precipitation temperature is 50°–90° C. and an increase in viscosity occurs after at most 25% of the duration of precipitation. The pH value is adjusted to ≦6, preferably 3.5, once a silica content of greater than 120 g/l or greater than 150 g/l, preferably ≧160 g/l to 240 g/l, has been reached, the solid is separated by filtration, washed, dried and ground. The precipitated silica has a BET surface area of 10– 130 m$^2$/g, a CTAB surface area of 10–70 m$^2$/g, an average particle diameter of 5–20 μm, a Cu abrasion value in a 10% glycerol dispersion of 4–50 mg, and thickening behavior in a CMC solution (20% dispersion) of 300–3500 mPa·s.

Chamber presses, belt filters or membrane filter presses, all known in the art, may be used for filtration.

A circulating air dryer, Büttner dryer, flow dryer or similar dryer, all known in the art, may be used for drying.

The liquefied filter cake may be dried in a spray dryer.

The filter cake may be subjected to mill drying without liquefaction.

All equipment and apparatus used were conventional and known in the art.

The advantage of the process according to the present invention is that the abrasive properties of the precipitated silica (and thus of the finished paste when used in toothpastes) may be adjusted over a wide range with elevated solids contents in the precipitation suspension, slight water retention in the filter cake, and consequently the use of less energy for drying. The degree of abrasion may here be purposefully adjusted by varying the solids content of the precipitation suspension, wherein accompanying precipitation parameters, such as for example temperature, pH value or rate of addition of reactants, allow further variation in terms of thickening behavior, refractive index etc. Despite the variation in solids contents, they are in the present precipitation process in principle at a very high level (≧120 g/l, preferably ≧160 g/l to 240 g/l).

Precipitated silica produced using the process according to the present invention may be used as an abrasive or thickening component in toothpaste formulations. A further possible application is use as a polishing or grinding agent. The precipitated silica produced according to the invention may preferably be used as an abrasive silica in toothpastes.

The following examples serve to illustrate the present invention:

EXAMPLE 1

Figure 1:
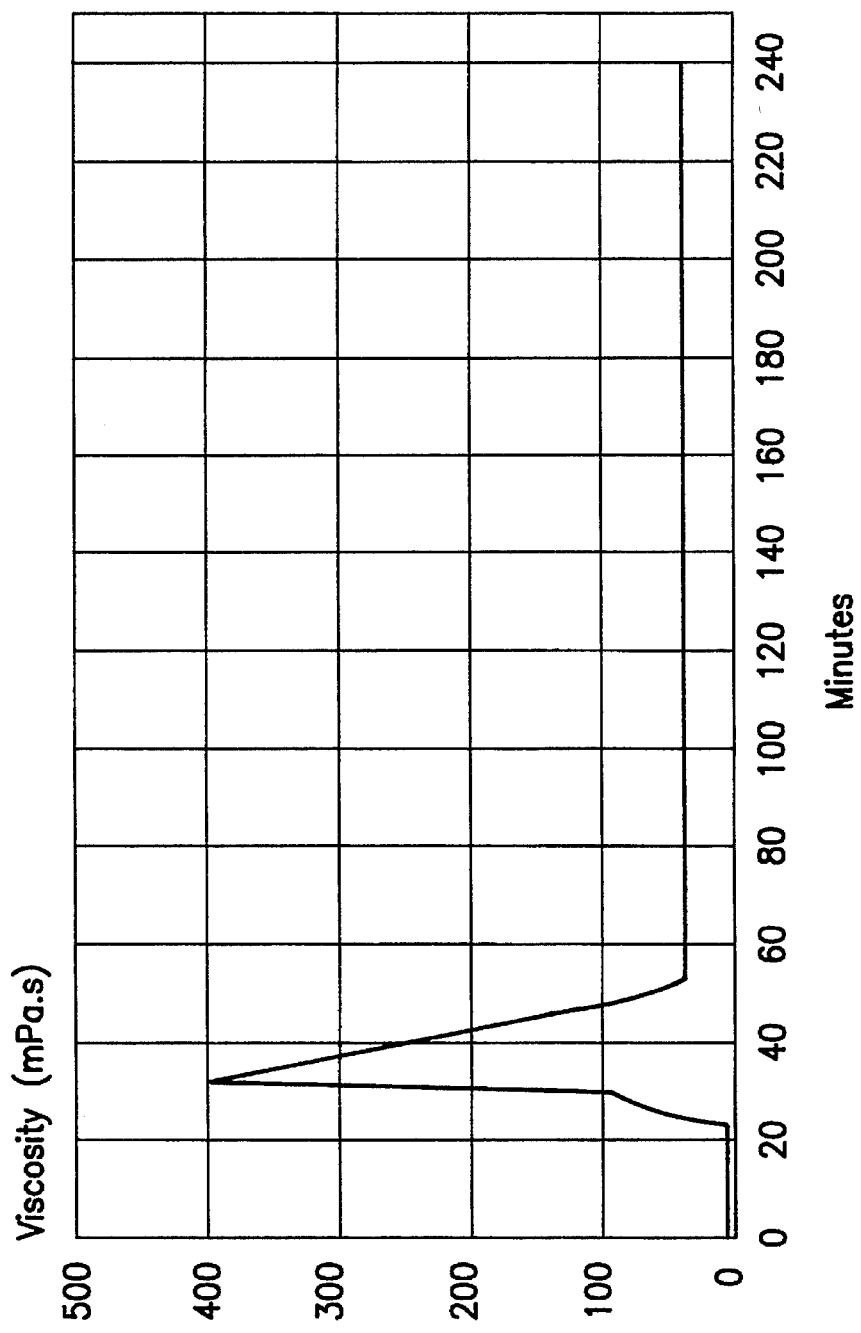
FIGS. 1–5 are graphs of the viscosity curves of the abrasive silicas of Examples 1–5 respectively.

12.8 l of water are introduced into an indirectly heated 50 l precipitation vessel and heated to 85° C. while being stirred. The pH is initially adjusted to 8.5 while maintaining this temperature by adding a little water glass solution (weight modulus 3.4:1=26.8% SiO$_2$ and 7.85% Na$_2$O; density 1.352 g/ml). Precipitation is then performed for 240 minutes by simultaneously adding 56.5 ml/min of water glass (composition as stated above) and a sufficient quantity of (50%) sulfuric acid to ensure that the pH is held constant at 8.5. This suspension is then acidified to pH 3.5 with (50%) sulfuric acid. The silica content of the suspension is 171 g/l. The viscosity curve during precipitation is shown in FIG. 1.

The silica obtained is separated from the suspension using a vacuum filter, the filter cake washed with water, dried at 105°–110° C. and ground in a laboratory pin mill.

EXAMPLE 2

Figure 2:
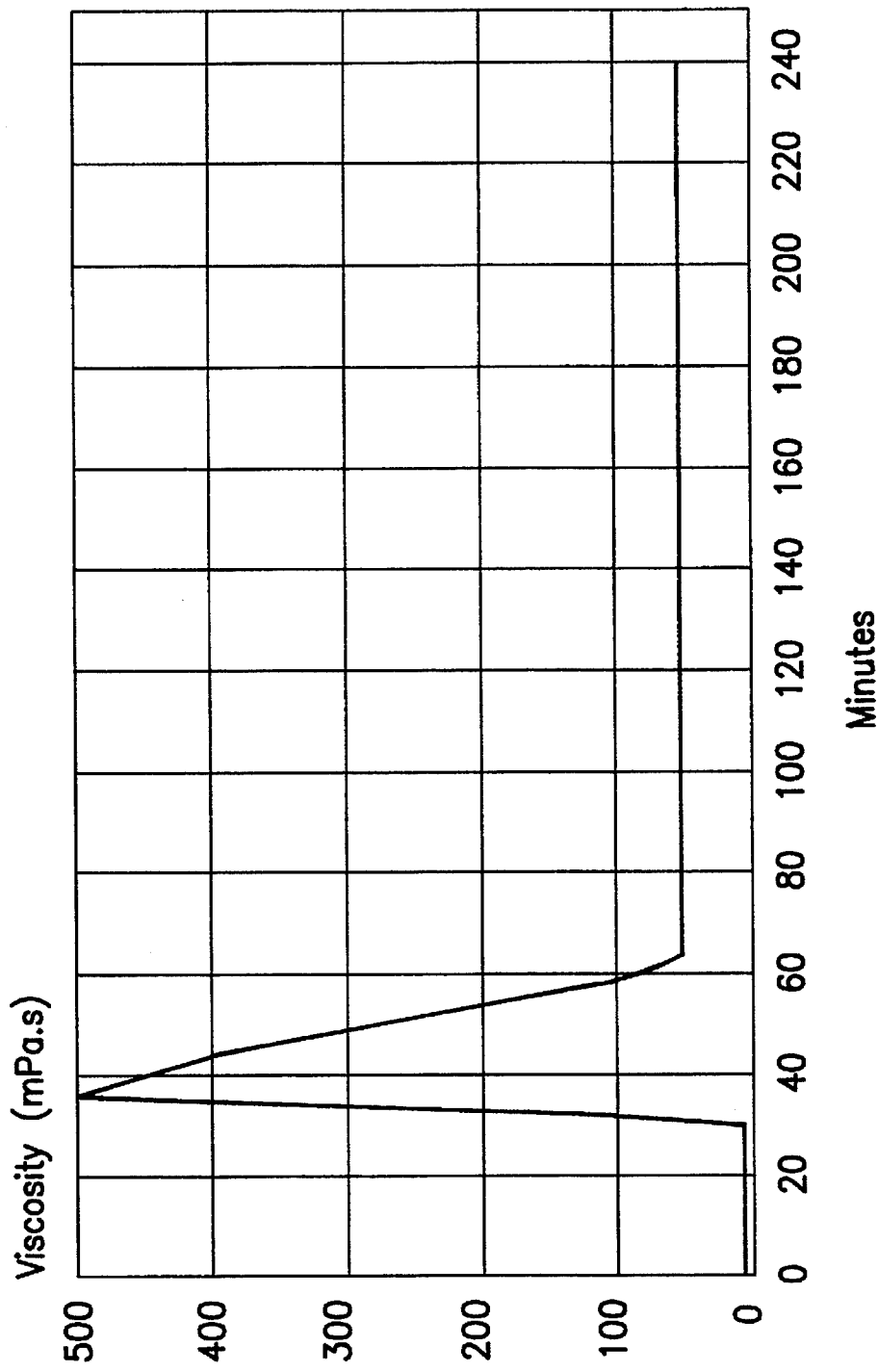

The same procedure is used as in Example 1 with the difference that the pH of the initial amount of water is adjusted to pH 10.7 with water glass solution and this pH is maintained during the simultaneous addition of water glass and sulfuric acid. The silica content of the suspension is 173 g/l. The viscosity curve during precipitation is shown in FIG. 2.

EXAMPLE 3

Figure 3:
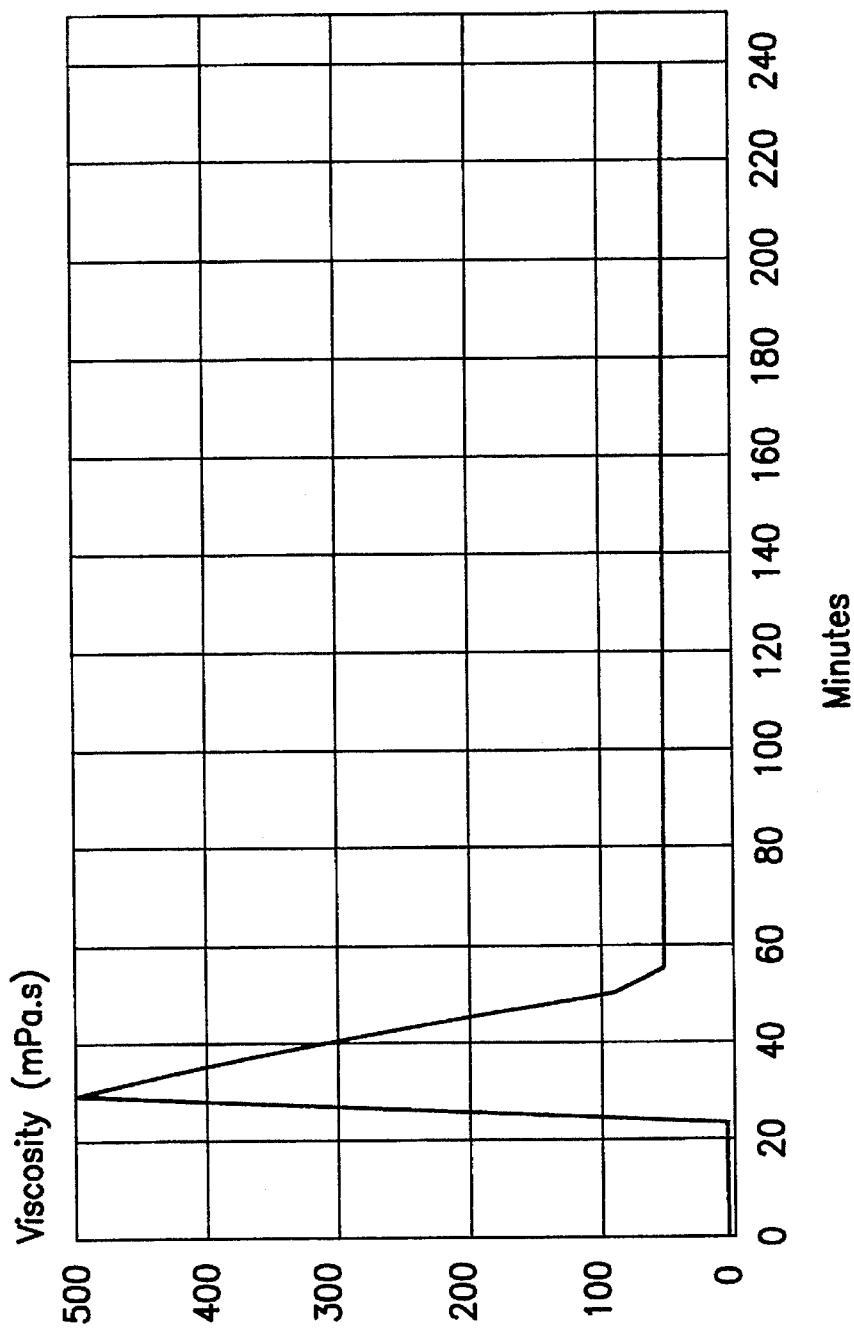

The same procedure is used as in Example 2; the only difference is that the silica content of the suspension is raised to 210 g/l by using increased quantities of water glass (96.1 ml/min) and sufficient sulfuric acid that the pH is maintained at 10.7 during the precipitation. The viscosity curve during precipitation is shown in FIG. 3.

EXAMPLE 4

Figure 4:
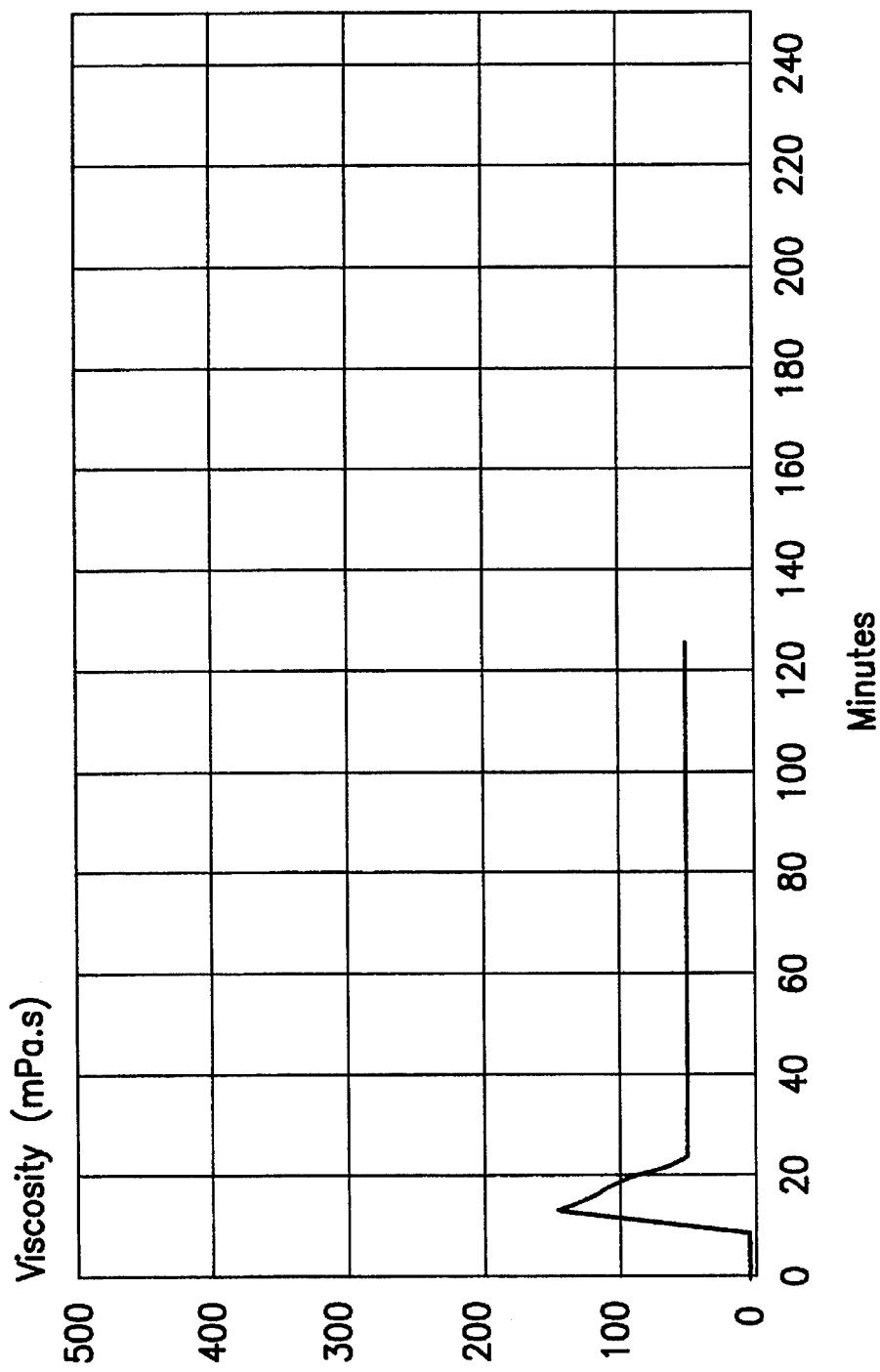

The same procedure is used as in Example 1 with the difference that the pH is held constant at 7 by adding water glass at a rate of 56.5 ml/min and sufficient (50%) sulfuric acid. Duration of precipitation is 126 min. After subsequent acidification to pH 3.5, a silica content of 125 g/l is found. The viscosity curve during precipitation is shown in FIG. 4.

EXAMPLE 5

Figure 5:
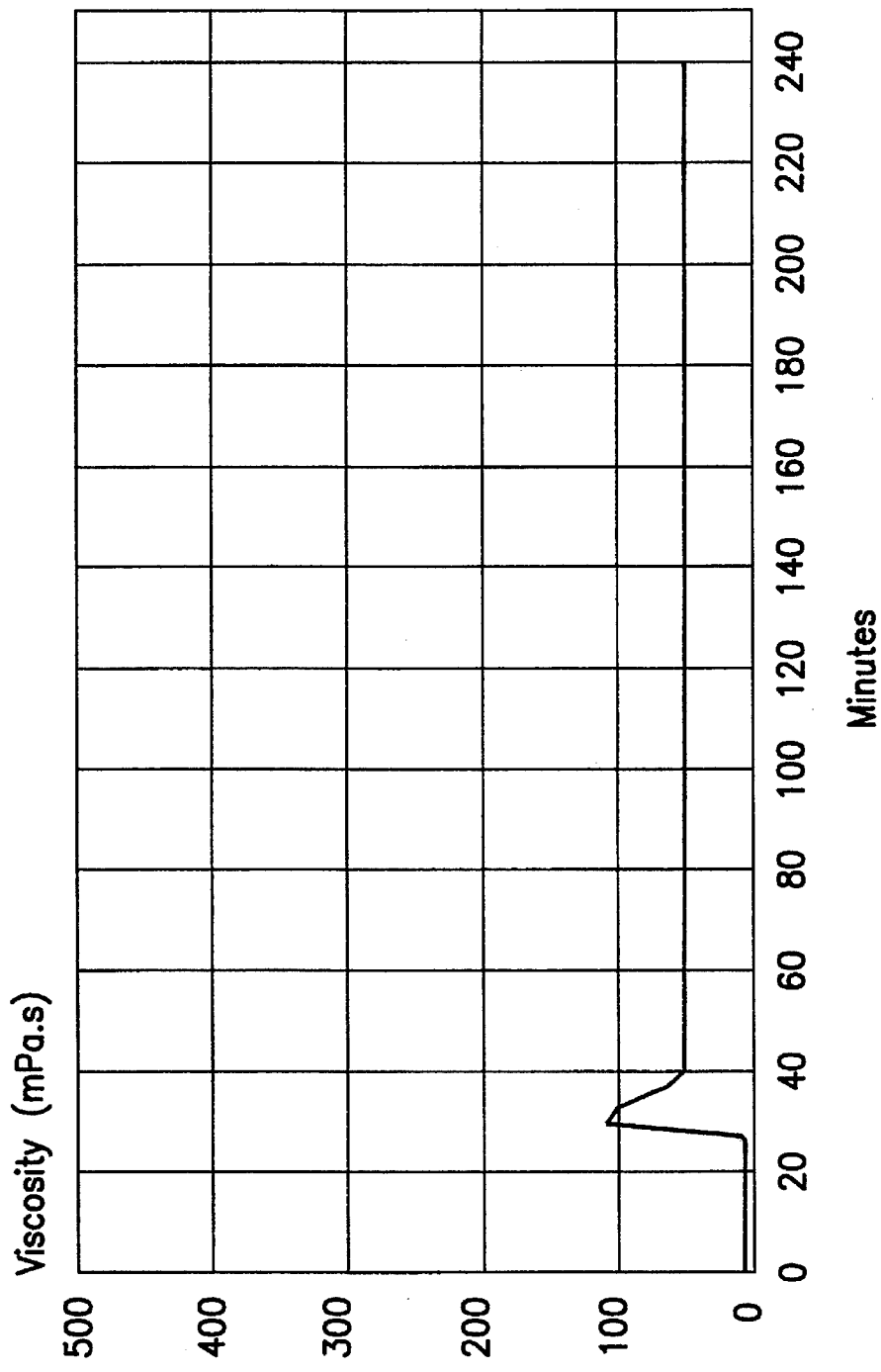

The same procedure is used as in Example 1, wherein a water glass with a weight modulus of 2.5 (20.44% $SiO_2$ and 8.18% $Na_2O$, d=1.3012 g/ml) is used and a silica content of 160 g/l in the suspension is achieved by raising the water glass feed rate to 107.3 ml/min and the $H_2SO_4$ feed rate to 26.33 ml/min. The viscosity curve during precipitation is shown in FIG. 5.

The physical, chemical and applicational data relating to the precipitated silicas obtained according to the present invention are shown in table 1.

TABLE

| Example | | 1 | 2 | 3 | 4 | 5 |
| --- | --- | --- | --- | --- | --- | --- |
| CTAB surface area | m²/g | 32 | 45 | 22 | 55 | 25 |
| BET surface area | m²/g | 37 | 130 | 115 | 65 | 32 |
| C.C. average particle size | μm | 12.8 | 11.7 | 13.8 | 12.5 | 14.1 |
| Cu abrasion | mg | 17 | 9 | 42 | 16 | 50 |
| CMC thickening | mPa · s | 900 | 2100 | 440 | 3200 | 420 |
| Moisture, 2 h at 105° C. | % | 3.5 | 3.8 | 4.0 | 3.2 | 3.9 |
| Conductivity | μS/cm | 70 | 40 | 80 | 110 | 100 |
| Ignition loss | % | 3.0 | 4.6 | 4.7 | 3.2 | 2.8 |
| Total duration of precipitation G | min | 240 | 240 | 240 | 126 | 240 |
| Viscosity increase point V | min | 24 | 30 | 23 | 9 | 27 |
| Percentage proportion of V to G | % | 10 | 12.5 | 9.6 | 7 | 11.3 |

The methods used in the table are as follows:

Determination of the specific nitrogen surface area (BET) is performed according to Brunauer-Emmet-Teller using the AREA-meter apparatus from Ströhlein. Determination is performed according to DIN (German Industrial Standard) ISO 5794/1, annex D. The original method was first described in *Journal of the American Chemical Society* (1938), volume 60, page 309. The conditioning temperature is 160° C. for 1 hour.

The CTAB surface area is determined by the adsorption of cetyltrimethylammonium bromide at pH 9 (c.f. Jay, Janzen & Kraus in *Rubber Chemistry and Technology* (1971), volume 44, page 1287).

Particle distribution is determined using the model TA II Coulter Counter from Coulter Electronics. The 100 μm capillary is used.

Abrasive properties are determined using the Cu abrasion method in a 10% glycerol dispersion (153 g of anhydrous glycerol into which 17 g of silica have been dispersed for 12 min at 1,500 rpm using a paddle stirrer). Abrasion is measured from 50,000 back and forth strokes with nylon brushes on Cu sheet (electrolyte copper) in the above dispersion. Cu abrasion is determined by differential weighing. Reference: Pfrengle, *Fette, Seifen, Anstrichmittel* (1961), volume 63, pages 445–451, and Reng, Dany *Parfümerie und Kosmetik* (1978), volume 59, pages 37–45.

Thickening behavior is determined at 20% in a carboxymethyl cellulose solution (50 g PEG 400, 1 kg 87% glycerol, 25 g AKU CMC L2 855, 925 g water). The test solution, which must be at least one day old but no more than 2 weeks old, is combined with silica, dispersed and the viscosity determined (Brookfield RVT, spindle 5, 10 rpm, value after 1 minute). The mixture, which is maintained at a temperature of 25° C., is measured immediately, after 0.5 h and after 24 h. The latter is the actual measurement.

Moisture content (2 h, 105° C. DIN ISO 787 part 2), conductivity (4%), ignition loss (2 h at 1000° C., analogous to DIN 55 921) are also determined.

Further variations and modifications of the foregoing will be apparent to those skilled in the art and such variations and modifications are attended to be encompassed by the claims that are appended hereto.

German Priority Application P 43 26 576.6, filed on Aug. 7, 1993, and German Priority Application P 44 23 493.7, filed on Jul. 5, 1994, are relied on and incorporated by reference.

What is claimed is:

1. A process for the production of a precipitated silica, said process comprising simultaneously adding alkali silicate with a weight modulus $SiO_2$:alkali oxide=2.5–3.9:1 and a mineral acid to an initial amount of water, which has been adjusted to a pH value of 7.0 to 9.9 or 10.0 to 10.7 by the addition of water glass, to form a mixture, holding constant the pH value of said mixture between 7.0 and 9.9 or 10.0 to 10.7 during the addition of said alkali oxide and mineral acid, wherein the initial precipitation temperature is 50°–90° C. and an increase in viscosity occurs after at most 25% of the duration of precipitation, adjusting the pH value to less than or equal to 6 from said pH value of 7.0 to 9.9 once a silica content of greater than 120 g/l has been reached or adjusting the pH value to less than or equal to 6 from said pH value of 10.0 to 10.7 once a silica content of greater than 150 g/l has been reached; wherein said precipitated silica has a BET surface area of 10–130 $m^2/g$, a CTAB surface area of 10–70 $m^2/g$, an average particle diameter of 5–20 μm, a Cu abrasion value in a 10% glycerol dispersion of 4–50 mg and thickening behavior in a CMC solution (20% dispersion) of 300–3500 mPa·s.

2. The process according to claim 1, further comprising separating said precipitated silica by filtration.

3. The process according to claim 2, further comprising washing said precipitated silica after filtration.

4. The process according to claim 3, further comprising drying said precipitated silica after washing.

5. The process according to claim 4, further comprising grinding said precipitated silica after drying.

6. The process according to claim 1, wherein said pH value is adjusted from a pH value of 10.0 to 10.7 once a silica content of 160–240 g/l has been reached.

7. The process according to claim 1, wherein said pH value is adjusted to 3.5 from said pH value of 7.0 to 9.9 once a silica content of greater than 120 g/l has been reached or said pH value is adjusted to 3.5 from said pH value of 10.0 to 10.7 once a silica content of greater than 150 g/l has been reached.

8. The process according to claim 1, wherein said process comprises a single precipitation stage.

9. The process according to claim 1, wherein said process does not involve the addition of electrolytes.

10. The process according to claim 8, wherein said process occurs at a simultaneously elevated space-time yield.

11. The process according to claim 1, wherein said process consists essentially of simultaneously adding alkali silicate with a weight modulus $SiO_2$:alkali oxide=2.5–3.9:1 and a mineral acid to an initial amount of water, which has been adjusted to a pH value of 7.0 to 9.9 or 10.0 to 10.7 by the addition of water glass, to form a mixture, holding constant the pH value of said mixture between 7.0 and 9.9 or 10.0 to 10.7 during the addition of said alkali oxide and mineral acid, wherein the initial precipitation temperature is 50°–90° C. and an increase in viscosity occurs after at most 25% of the duration of precipitation, adjusting the pH value to less than or equal to 6 from said pH value of 7.0 to 9.9 once a silica content of greater than 120 g/l has been reached or adjusting the pH value to less than or equal to 6 from said pH value of 10.0 to 10.7 once a silica content of greater than 150 g/l has been reached.

* * * * *